(12) United States Patent
Nistico et al.

(10) Patent No.: US 9,380,287 B2
(45) Date of Patent: Jun. 28, 2016

(54) HEAD MOUNTED SYSTEM AND METHOD TO COMPUTE AND RENDER A STREAM OF DIGITAL IMAGES USING A HEAD MOUNTED DISPLAY

(71) Applicant: SENSOMOTORIC INSTRUMENTS GESELLSCHAFT FUR INNOVATIVE SENSORIK MBH, Teltow (DE)

(72) Inventors: Walter Nistico, Berlin (DE); Jan Hoffmann, Kleinmachnow (DE); Eberhard Schmidt, Kleinmachnow (DE)

(73) Assignee: SENSOMOTORIC INSTRUMENTS GESELLSCHAFT FUR INNOVATIVE SENSORIK MBH, Teltow (DE)

( * ) Notice: Subject to any disclaimer, the term of this patent is extended or adjusted under 35 U.S.C. 154(b) by 0 days.

(21) Appl. No.: 14/439,553

(22) PCT Filed: Sep. 2, 2013

(86) PCT No.: PCT/EP2013/068113
§ 371 (c)(1),
(2) Date: Apr. 29, 2015

(87) PCT Pub. No.: WO2014/033306
PCT Pub. Date: Mar. 6, 2014

(65) Prior Publication Data
US 2015/0288944 A1 Oct. 8, 2015

(30) Foreign Application Priority Data

Sep. 3, 2012 (EP) ..................................... 12182804

(51) Int. Cl.
*H04N 13/00* (2006.01)
*H04N 13/04* (2006.01)
(Continued)

(52) U.S. Cl.
CPC ........ *H04N 13/0022* (2013.01); *G02B 27/0093* (2013.01); *G02B 27/0172* (2013.01); *G06F 3/013* (2013.01); *H04N 13/044* (2013.01); *H04N 13/0484* (2013.01); *G02B 2027/0178* (2013.01)

(58) Field of Classification Search
CPC .. G06F 3/013; H04N 13/0022; H04N 13/044; H04N 13/0484
See application file for complete search history.

(56) References Cited

U.S. PATENT DOCUMENTS 6,449,309 B1 9/2002 Tabata
6,545,650 B1 4/2003 Yamada et al.
(Continued)

FOREIGN PATENT DOCUMENTS

CA 2 750 287 A1 11/2011
EP 2 439 611 A1 4/2012

OTHER PUBLICATIONS

International Search Report and Written Opinion for PCT/EP2013/068113 dated Nov. 4, 2013.
(Continued)

*Primary Examiner* — Gerald Johnson
(74) *Attorney, Agent, or Firm* — Sughrue Mion, PLLC

(57) ABSTRACT

The invention relates to a head mounted system (10) comprising a binocular eye tracking system (14a, 14b) comprising at least a first camera (14a) arranged for acquiring a user's left eye (16a) and at least a second camera (14b) arranged for acquiring a user's right eye (16b), a head mounted display (10) comprising a first displaying means (18a) for presenting an image to a user's left eye (16a), a second displaying means (18b) for presenting an image to a user's right eye (16b), a processing unit (24, 24a, 24b) designed to process images from the eye tracking system (14a, 14b) and calculate at least a 3D position of the left (16a) and the right eye (16b) and an orientation vector of the left (16a) and the right eye (16b) and to compute and render a stream of digital images to be projected onto the user's left and right eye (16a, 16b) by means of the head mounted display, wherein the processing unit (24, 24a, 24b) is further designed to consider the 3D position of the left and the right eye (16a, 16b) and the orientation of the left and the right eye (16a, 16b) when computing and rendering the stream of digital images. The invention further relates to a method to compute and render a stream of digital images using a head mounted display.

30 Claims, 6 Drawing Sheets

Figure 1A:
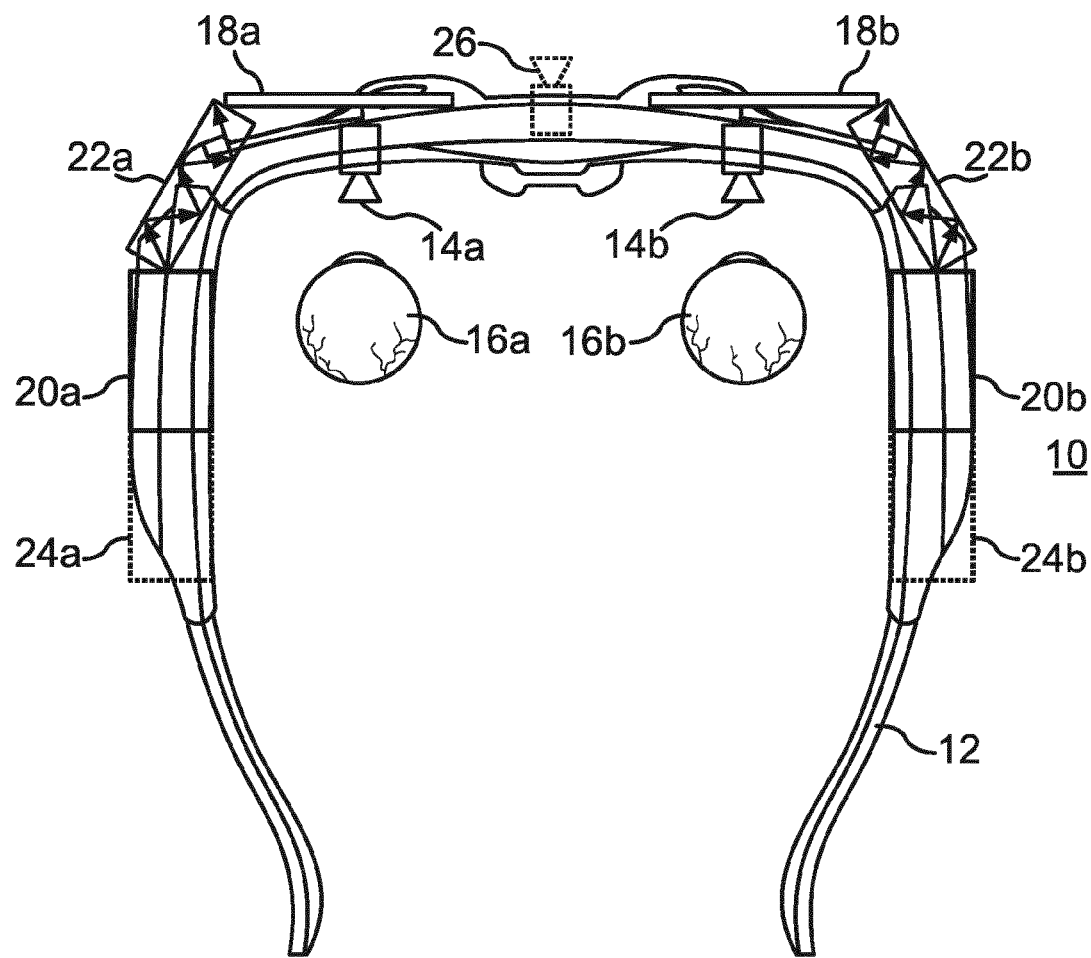

(51) Int. Cl.
*G02B 27/01* (2006.01)
*G02B 27/00* (2006.01)
*G06F 3/01* (2006.01)

(56) References Cited

U.S. PATENT DOCUMENTS

| | | | |
|---|---|---|---|
| 2009/0304232 A1* | 12/2009 | Tsukizawa | A61B 3/113 382/103 |
| 2009/0315978 A1* | 12/2009 | Wurmlin | G06T 5/005 348/43 |
| 2011/0075257 A1 | 3/2011 | Hua et al. | |
| 2012/0127284 A1 | 5/2012 | Bar-Zeev et al. | |
| 2013/0114135 A1* | 5/2013 | Lin | H04N 13/0409 359/464 |

OTHER PUBLICATIONS

International Preliminary Report on Patentability and Written Opinion for PCT/EP2013/068113 dated Jan. 22, 2015.

Shih Sheng-Wen et al: "A novel approach to 3-D gaze tracking using stereo cameras", IEEE Transactions on Systems, Man and Cybernetics. Part B:Cybernetics, IEEE Service Center, Piscataway, NJ, US, vol. 34, No. 1, Feb. 1, 2004, pp. 234-245.

Hong Hua et al: "Video-based eyetracking methods and algorithms in head-mounted displays", Optics Express, vol. 14, No. 10, May 15, 2006, p. 4328.

* cited by examiner

HEAD MOUNTED SYSTEM AND METHOD TO COMPUTE AND RENDER A STREAM OF DIGITAL IMAGES USING A HEAD MOUNTED DISPLAY

CROSS REFERENCE TO RELATED APPLICATIONS

This is a National Stage of International Application No. PCT/EP2013/068113 filed Sep. 2, 2013, claiming priority based on European Patent Application No. 12 182 804.0 filed Sep. 3, 2012, the contents of all of which are incorporated herein by reference in their entirety.

DESCRIPTION

The present invention relates to a head mounted system comprising a binocular eye tracking system comprising at least a first camera arranged for acquiring a user's left eye, at least a second camera arranged for acquiring a user's right eye. The head mounted system further comprises a head mounted display comprising first displaying means for presenting an image to a user's left eye and second displaying means for presenting an image to a user's right eye. The head mounted system further comprises a processing unit designed to process images from the eye tracking system and calculate at least a 3D position of the left and the right eye and an orientation vector of the left and the right eye. The processing unit is further designed to compute and render a stream of digital images to be projected onto the user's left and right eye by means of the head mounted display. It further relates to a method to compute and render a stream of digital images using such a head mounted system.

Such head mounted systems are used for doing eye tracking, oculometrics, biometrics and position and motion measurement in order to measure and classify as fully as possible human behaviour in a free range movement setup.

US 2012/0179369 describes a personal navigation device using a head mounted device (HMD) and incorporating a processor. It uses head orientation and a portable coordinate position sensor (GPS). U.S. Pat. No. 8,004,765 describes an optical device with a first light transmitting substrate, a transparent layer having at least two major surfaces where light waves travel by total internal reflection. U.S. Pat. No. 7,672,055 describes an optical device comprising a light-transmitting substrate having at least two major surfaces parallel to each other and edges, a first optical element for coupling light waves located in a field-of-view into said substrate by internal reflection, and a second optical element for coupling said trapped light waves out of said substrate, wherein at least one of said major surfaces is coated with an angular sensitive coating. From US 2010/0171680 an electro-optical system of two units is known, including an HMD and a separate control unit, which communicates by a narrowband wireless channel. U.S. Pat. No. 8,189,263 describes an optical apparatus for HMD, comprising a waveguide, a 1D-array of in-coupling mirrors and a 2D-array of out-coupling mirrors. U.S. Pat. No. 6,433,760 describes a device which integrates a head mounted display with an eye tracking device. It represents a very specific eye tracking technology which uses four light sources to generate four glints, an eye tracker and an HMD projection mechanism sharing the same optical path by using a beam splitter. U.S. Pat. No. 4,958,925 teaches eye movement detection using orthogonal pairs of light emitting elements and light detecting elements. U.S. Pat. No. 5,331,149 describes the combination of a display with photodetector array. The light emitting and light detecting elements are co-located and the light emitted towards and reflected from the eyes shares the same optical path. The display can be helmet mounted. U.S. Pat. No. 7,783,077 teaches a method for tracking movement of an eye of an operator comprising an eye camera, a processing device, a custom template which resembles at least a portion of said eye comprising shape, size and illumination. WO 2011/156195 deals with a speech generation device comprising a head mounted display unit configured as an item to be worn on a user's head, the head mounted display unit including a display device for displaying one or more images within a field of view of the user, a speaker for generating audio outputs, and a processing unit communicatively coupled to the head mounted display unit and speaker. Eye tracking is optional and can only be used as a cursor to control speech generation. U.S. Pat. No. 7,522,344 teaches a projection-based head-mounted display device with eye tracking. It uses multiple light sources to illuminate the eye and create a polygon of multiple glints, dark and bright pupil alternating, optics to provide optical path for head mounted display path and eye tracker path, a first and second hot mirror positioned in the eye tracker path to reflect the infrared light and transmit visible light via an interface to an external controller. It relates to one particular technical solution where an HMD and eye tracking (ET) device share the same optical path for projecting images towards the eyes and observing the eyes to do eye tracking.

This technology uses hot mirrors and alternating off-axis/on-axis illumination to achieve dark and bright pupil effect for detection. Another device for combining HMD and ET is known from U.S. Pat. No. 8,235,529. It describes a method to switch the device between an "active", high power mode of operation and a "locked", low power state by displaying a smooth moving object and tracking the eye path which must substantially follow the moving object to "unlock" the device and switch mode. This matching is also used to calibrate a transformation of the gaze path calculated by the eye tracker by determining an offset, scaling and rotational adjustment. EP 2 499 962 A1 relates to a head mounted eye tracking device in the form of goggles. It does not include an HMD.

U.S. Pat. No. 8,130,260 B2 discloses a system for a 3D display that includes at least one eye piece having first and second eye piece sockets, having a first display contained in said first eye piece socket associated with the first eye, two eye cameras mounted such that a first eye camera tracks eye reference points of said first eye and a second eye camera tracks reference points of a second eye, a processor for providing overall control of said at least one eye piece, a second display, and a main processor. Signals are transmitted between said main processor and said at least one eye piece, wherein said two eye cameras track said reference points, said eye piece transceiver transmits said reference points to the main processor via said main transceiver. Said main processor generates image data based on said reference points and transmits said image data to said displays to produce a 3D image. This document has been used to formulate the preamble of the independent claims of the present application.

US 2010/0322479 A1 deals with systems and methods for 3D target location. Thereby, a target is imaged in a three-dimensional space using two or more video cameras. A 3D image space combined from two video cameras of the two or more video cameras is displayed to a user using a stereoscopic display. A right eye and a left eye of the user are imaged as the user observes the target in the stereoscopic video display, a right gaze line of the right eye and a left gaze line of the left eye are calculated in the 3D image space, and a gaze point in the 3D image space is calculated as the intersection of the right gaze line and the left gaze line using a binocular eye tracker. A real target location is determined by translating the gaze point in the 3D image space to the real target location in the 3D real space from the locations and the positions of the two video cameras using a processor. Systems using eye mounted displays are known from US 2009/0189974 A1. This document teaches a display device which is mounted on and/or inside the eye. The eye mounted display contains multiple sub-displays, each of which projects light to different retinal positions within a portion of the retina corresponding to the sub-display. The projected light propagates through the pupil but does not fill the entire pupil. In this way, multiple sub-displays can project their light onto the relevant portion of the retina. Moving from the pupil to the cornea, the projection of the pupil onto the cornea is referred to as the corneal aperture. The projected light propagates through less than the full corneal aperture. The sub-displays use spatial multiplexing at the corneal surface. Various electronic devices interface to the eye mounted display. US 2012/0200676 A1 is directed to a hybrid stereo image/motion parallax system that uses stereo 3D vision technology for presenting different images to each eye of a viewer, in combination with motion parallax technology to adjust each image for the positions of a viewer's eyes. In this way, the viewer receives both stereo cues and parallax cues as the view moves while viewing a 3D scene, which tends to result in greater visual comfort/less fatigue to the viewer. Also described is the use of goggles for tracking viewer position, including training a computer vision algorithm to recognize goggles instead of only heads/eyes.

Further relevant prior art is known from the following publications: "Interacting with eye movements in virtual environments" by Vildan Tanriverdi and Robert J. K. Jacob, published on *Proceedings of the SIGCHI conference on Human Factors in Computing Systems in* 2000 "Binocular eye tracking in virtual reality for inspection training" by Andrew T. Duchowsky, Vinay Shivashankaraiah and Tim Rawls, published on *ETRA '00 Proceedings of the* 2000 *symposium on Eye tracking research & applications* in 2000. A master thesis entitled "Development of a head mounted device for point-of-gaze estimation in three dimensions" by Morten Lidegaard, the Maersk McKinney Moller Institute of University of Southern Denmark of Jun. 1, 2012 as well as a paper entitled "Eye tracking in advanced interface design" by Robert J. K. Jacob, published on *Virtual Environments and Advanced Interface Design* in 1995.

The object of the present invention is to further enhance the capabilities of a head mounted system as indicated in the preamble of claim 1. In the same way, it is a further object of the present invention to provide an improved method to compute and render a stream of digital images using a head mounted system.

These objects are solved by a head mounted system with the features of claim 1 and a method to compute and render a stream of digital images with the features of claim 27.

The present invention is based on the finding that known head mounted systems assume a standard fixed position of the eyes of a person to render the images as would be seen by this standard person. However, significant individual variations exist in intra-ocular distance and position of the eyes with respect to the nose. Some state of the art systems try to improve thereupon using some type of manual calibration procedure, which however is both very inaccurate and time consuming. Based thereon, in a head mounted system according to the present invention the processing unit is further designed to consider the 3D position of the left and the right eye and the orientation of the left and the right eye when computing and rendering the stream of digital images. This information is provided by the binocular eye tracking system.

Doing so, the digital images provided by the processing unit can be computed and rendered exactly fitting to the intra-ocular distance and position of the eyes with respect to the nose of an individual person. As a result, the 3D position of the virtual point of view used for left/right image rendering of the virtual reality 3D scene matches the exact positions of the user's eyes as measured by the binocular eye tracking system (instead of a standard fixed or manually calibrated intra-ocular distance as in state of the art devices). This reduces strain and dizziness and improves the depth perception.

In a preferred embodiment the head mounted system comprises wearing means and the processing unit is mechanically coupled to those wearing means. If the wearing means are further provided with an energy store like batteries or accumulators, a very high degree of freedom is achieved for the user.

Alternatively, the head mounted system can comprise wearing means and a data interface mechanically coupled to those wearing means, the processing unit being coupled with the data interface, especially wired or wireless. In this way, the head mounted system according to the present invention can use or access large computing units, which provide correspondingly large computing capabilities and are still designed such as to be worn by the user easily and without impairment. By means of the coupling with large processing units the calculations required with the present invention can be executed with particular speed and precision.

A particularly preferred embodiment is characterized in that the head mounted system comprises light guide means for projecting images onto said user's eyes which follow substantially separate optical paths as compared to the optical path used by the eye tracking system. Based on the different optical paths, in particular in connection with dark pupil technology, one achieves the advantage that one does not need a beam splitter, and light transmission is enhanced, achieving better signal to noise ratio in the images.

It has turned out to be advantageous when the processing unit is designed to calculate the 3D position of a point of regard, in particular the 3D position of the point of regard and the distances to each of the eyes, that the user is fixating using the 3D eye position of the left and the right eye and the orientation vectors of the left and the right eye. This allows to determine which part of the scene has to be rendered in focus, and which out of focus. Furthermore it is part of a GUI activation mechanism as described in further detail below. Based thereon, the present invention can provide an enhanced perception of depth since it exactly fits each individual.

Advantageously, the processing device is designed to estimate the 3D position of the point of regard as the closest point between the left and the right direction rays defined by the calculated 3D positions and orientation vectors of the left and the right eye. By knowing the point of regard an adaptation of the system to the individual person is possible. In this regard, it is advantageous when the processing unit is designed to filter the left and the right eye direction rays and positions through a mapping function, especially by applying an offset, a linear or a non-linear transformation.

It has turned out to be especially advantageous when the mapping function is the result of a calibration procedure calibrating the head mounted system for a specific user. In this regard, the processing unit can be designed to carry out the calibration procedure by showing through the head mounted display to the user virtual stimuli, in particular virtual targets, to be fixated and determining the difference between the point of regard calculated by the 3D positions and orientation vectors of the left and the right eye on the one side and the location of said virtual stimuli on the other side.

In this connection, the processing unit can be designed to provide said virtual targets (and/or stimuli) moving along a predetermined or random path. Alternatively, the processing unit can be designed to carry out the calibration procedure by continuously calculating over time the difference between the point of regard calculated by the 3D positions and orientation vectors of the left and the right eye on the one side and frequent objects of interest and/or visual anchors in the images projected on the head mounted display. By means of the last-mentioned variant, the calibration procedure can take place during the normal use of the head mounted system, wherein due to the continuous calculation an increasing reduction of the difference between the point of regard calculated by the 3D positions and the orientation vectors of the left and the right eye on the one side and the frequent objects of interest and/or visual anchors in the images on the other side can be achieved.

The processing unit can be further designed to calculate the intra-ocular distance and can be further designed to calculate based on the intra-ocular distance and the 3D positions of the left and the right eye the virtual points of view and to use these virtual points of view when rendering a pair of images for the left and the right eye for simulating a 3D virtual scene. This results in the advantage that the user will see the virtual scene from the point of view of his own eyes, not from the point of view of some standard population average or inaccurate manually calibrated estimate. This will match much more closely what he sees when looking at a real scene (not simulated), so the user's brain will find it more closely matching his expectations and the scene will appear more "natural" involving less strain and dizziness.

In an advantageous embodiment the processing unit is designed to determine based on the distance of the point of regard a region which is to be shown in focus in the rendered virtual image, wherein the processing unit is further designed to render the virtual images accordingly to simulate the depth of focus for the whole image which a human eye would observe if it were seeing a real object at the same 3D coordinates as the point of regard in a real scene. By calculating a focussing distance by vergence (by the eye tracker) it is possible to realistically simulate focussing accommodation by the user. Further, a depth of focus simulation is possible which follows where the user is actually looking in the virtual scene, instead of pre-defined focussing distance, thus simulating a user's own focus accommodation.

In this connection, the processing unit can be designed to render based on the 3D positions of the left and the right eye on the one side and the distance to said point of regard on the other side at least one augmented reality element which blends in with the scene as seen by a user wearing the head mounted system. In this connection a scene camera mounted on the wearing means can be used which provides images of the scene in front of the user. In this regard the scene camera can be used to perform object detection and recognition. Then some context specific information can be blended in using augmented reality to show to the user such information blended in with what the user sees. For example, a user might be looking at a text or road sign in a foreign language: The scene camera could acquire the images of the text, these being OCRed in the processing unit, then being machine-translated, and the translated text being shown in the augmented reality in virtual proximity of the original text. Or the user might be looking at a monument in a city, the monument being recognized by a software on the processing unit, and information about that document (history, art style, etc.) could be retrieved from a database and the text being displayed in the augmented reality in the form of a balloon near the object.

According to a particularly preferred embodiment, the processing unit is designed to render at least one virtual activation element to be shown in the images, especially the images of a scene, projected onto the user's eyes, the processing unit being further designed to activate a predetermined function associated with the virtual activation element if a predetermined activation condition is met.

While HMDs known from the prior art usually use touch or button interfaces to control the functionality, in the present invention a 3D graphic user interface (GUI) is provided where the eye tracking and depth estimation are used to activate elements in such a 3D GUI.

In this connection, it has turned out to be advantageous when the processing unit is designed to render said at least one virtual activation element as a finite, polygonal, 3D or 2D shape positioned at a predetermined position with a predetermined 3D orientation for a certain time in the scene. The processing unit can be designed to render said at least one virtual activation element with a predetermined colour and/or containing text and/or an image in itself and/or with varying degrees of transparency between none and fully transparent. Varying transparency is used to highlight or fade out activation elements which may be stacked at different virtual distances from the user. So for example, if the user focuses his gaze towards short distance activation elements, these will be made more opaque; if he then focuses towards far distance activation elements, those in front will be made translucent or even fully transparent so as not to occlude the clear sight of the activation elements which the user is currently focussing on.

With regard to the activation of the activation element, the processing unit can be designed such that the activation condition consists in the 3D point of regard entering a virtual space region defined by the activation element. Alternatively or additionally, the processing unit can be designed such that the activation condition consists in the 3D point of regard dwelling in the virtual space region defined by the activation element for a predetermined amount of time. Further, the processing unit can be designed such that the activation condition consists in the 3D point of regard entering and exiting the virtual space region defined by the activation element within a predetermined amount of time.

The processing unit can also be designed such that the activation condition consists in the 3D point of regard entering the virtual space region defined by the activation element and a subsequent blink within a predetermined time window being detected by the eye tracking system. The processing unit can also be designed such that the activation condition consists in the 3D point of regard entering the virtual space region defined by the activation element and a subsequent trigger event from an external interface is being activated. In this regard, the trigger event from an external interface can be one of the following: The pushing of a mechanical trigger, button or touch sensitive surface; the detection of a change in an electromyographic interface connected to the body of the user; the issuing of a voice command; a biological monitoring function reaching a threshold level, the biological monitoring function especially consisting in pulse/heart, blood pressure, a channel in an EEG interface; and/or a finger, hand or arm gesture detected by a gesture sensor. The usage of external activation signals can render activations easier in some contexts when available, for example clicking a button can be faster than letting the point of regard dwell within an activation element for a certain time. The use of biological signals allows the activation of certain elements only in combination with some predetermined emotional, mental or physical states.

Advantageously, the processing unit is designed to highlight and/or pre-activate a group of activation elements which lie at the same virtual distance based on an image disparity and a simulated depth of focus calculated from the 3D positions of the left eye, the right eye and the point of regard. By highlighting or pre-activating a group of activation elements it is possible to group the action by a common context, for example a group can be related to emails (e.g. open, compose, reply, reply all etc.). The pre-activation mechanism renders it easier to activate functions within a certain context than functions which are defined within another context (group), thus preventing accidental activations. Also pre-activation makes all the elements in a group more "visible" compared to elements in other groups (for example by making pre-activated elements opaque, and non-pre-activated elements transparent), and this again facilitates their activation and prevents accidental misactivations of elements in other groups.

With the present invention it is possible to design the processing unit such that it highlights a certain group of activation elements by substantially focussing all its elements, while all other activation elements in other groups are being rendered out of focus. Furthermore or alternatively, the processing unit can be designed to render all activation elements in other groups partially or completely transparent. This way, it is especially advantageous to a user to activate a desired group of activation elements dealing with related topics.

The preferred embodiments and advantages thereof described with regard to a head mounted system according to the invention correspondingly apply to the method according to the invention, wherein in particular the embodiments of the processing unit constitute steps of preferred embodiments of the method according to the invention.

In the following, advantageous embodiments of the present invention are described in more detail with reference to the accompanying drawings.

Figure 1B:
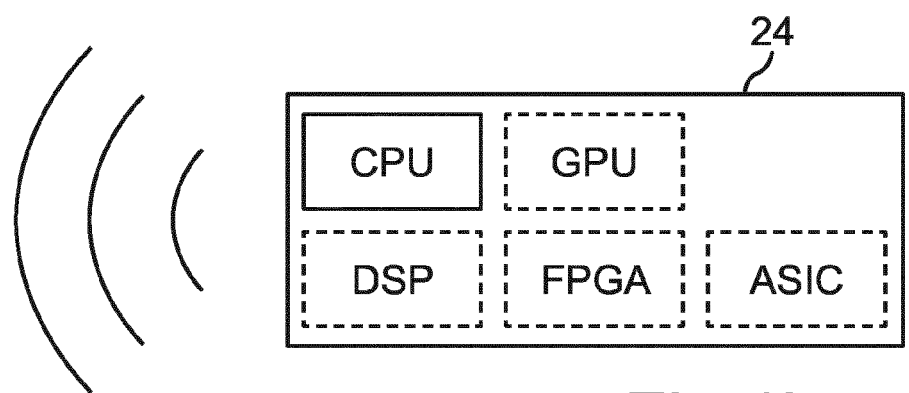
Figure 2:
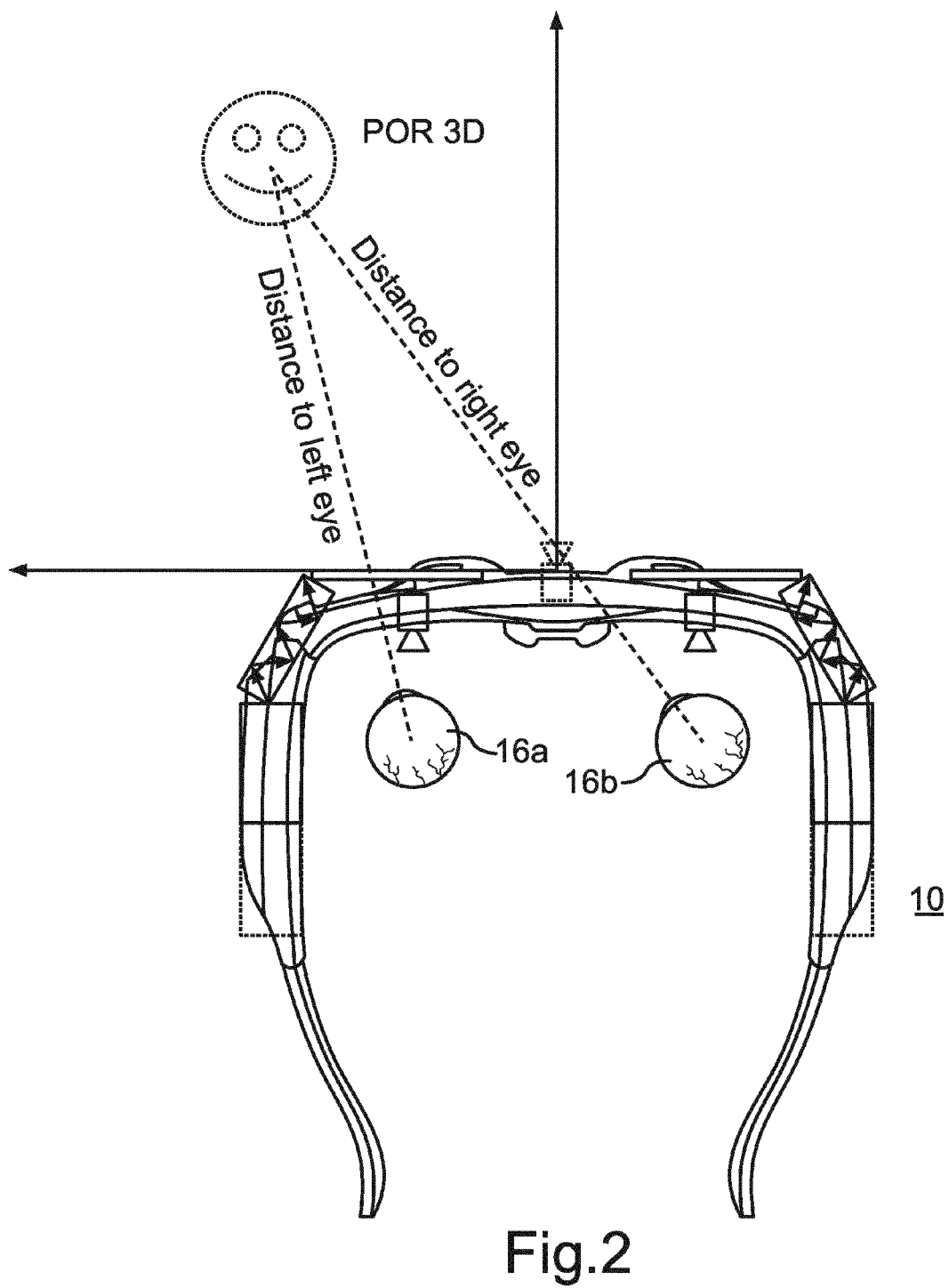
Figure 3:
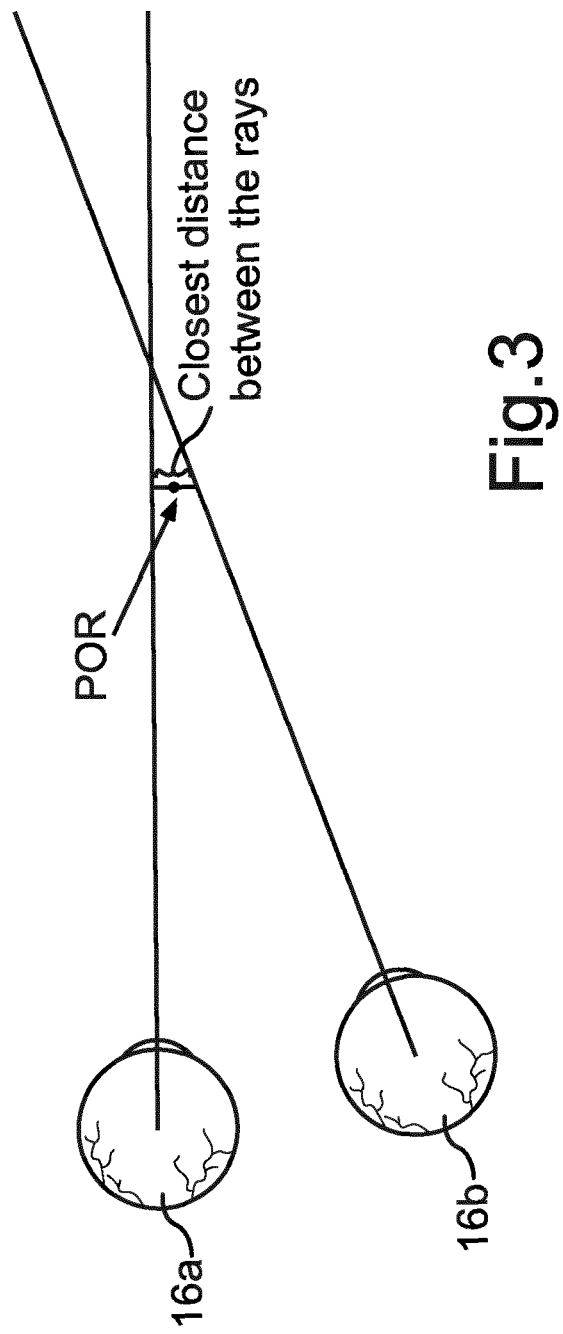
Figure 4:
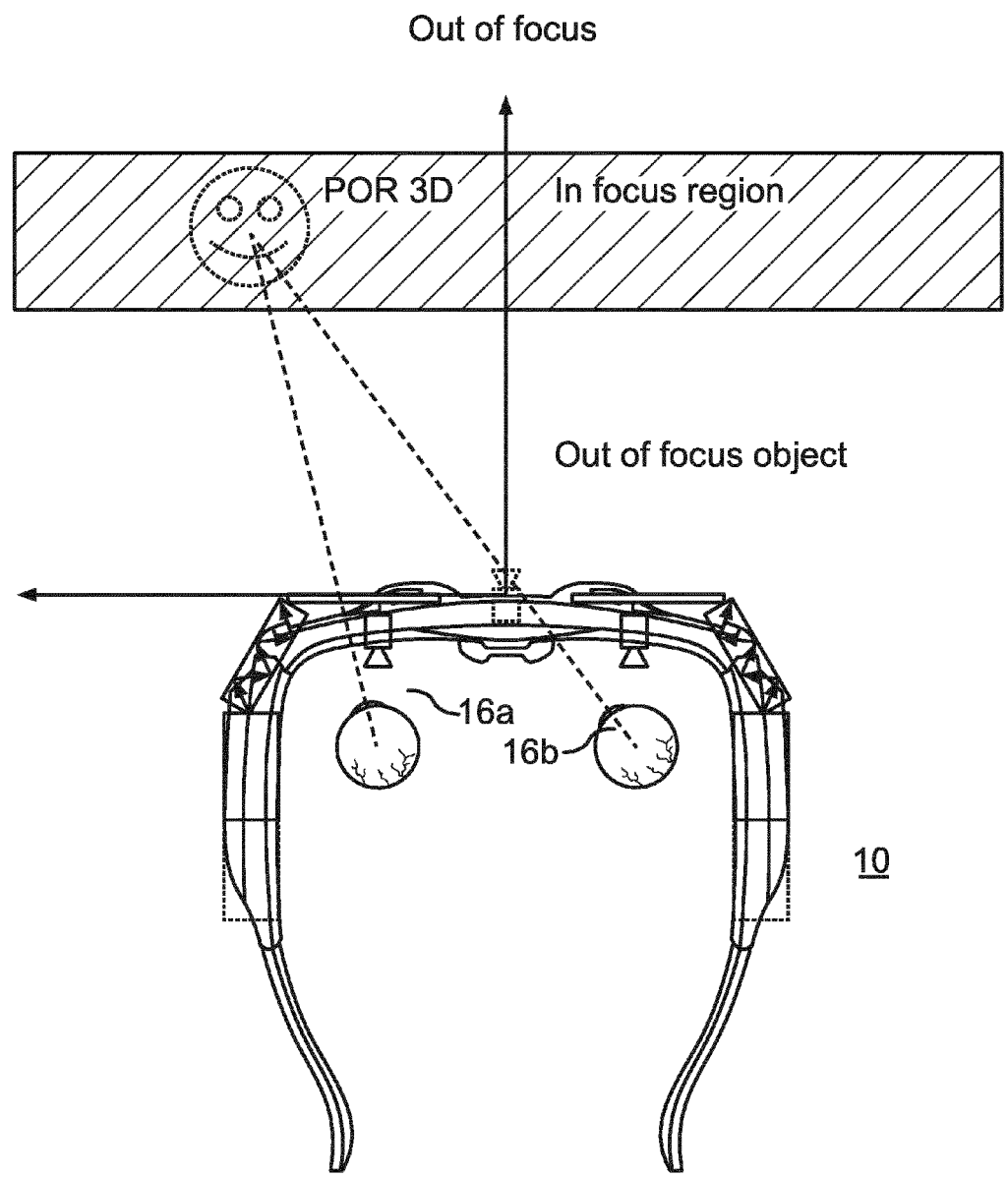
Figure 5:
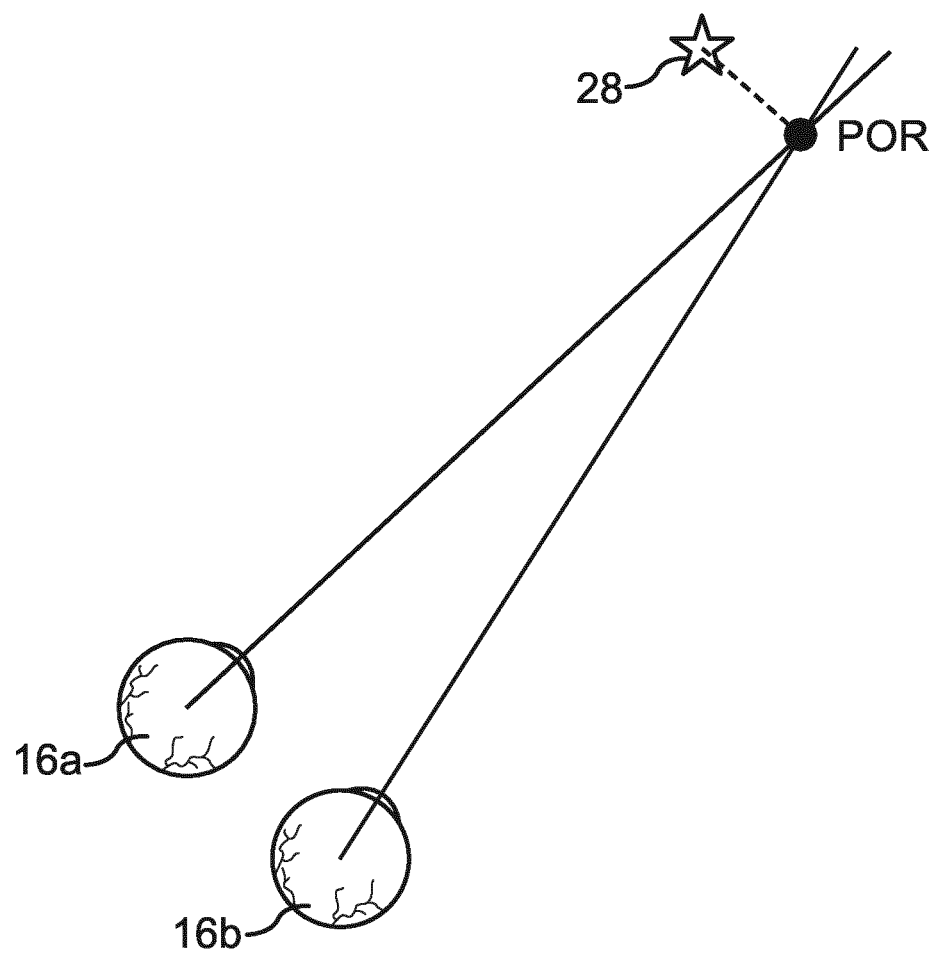
Figure 6:
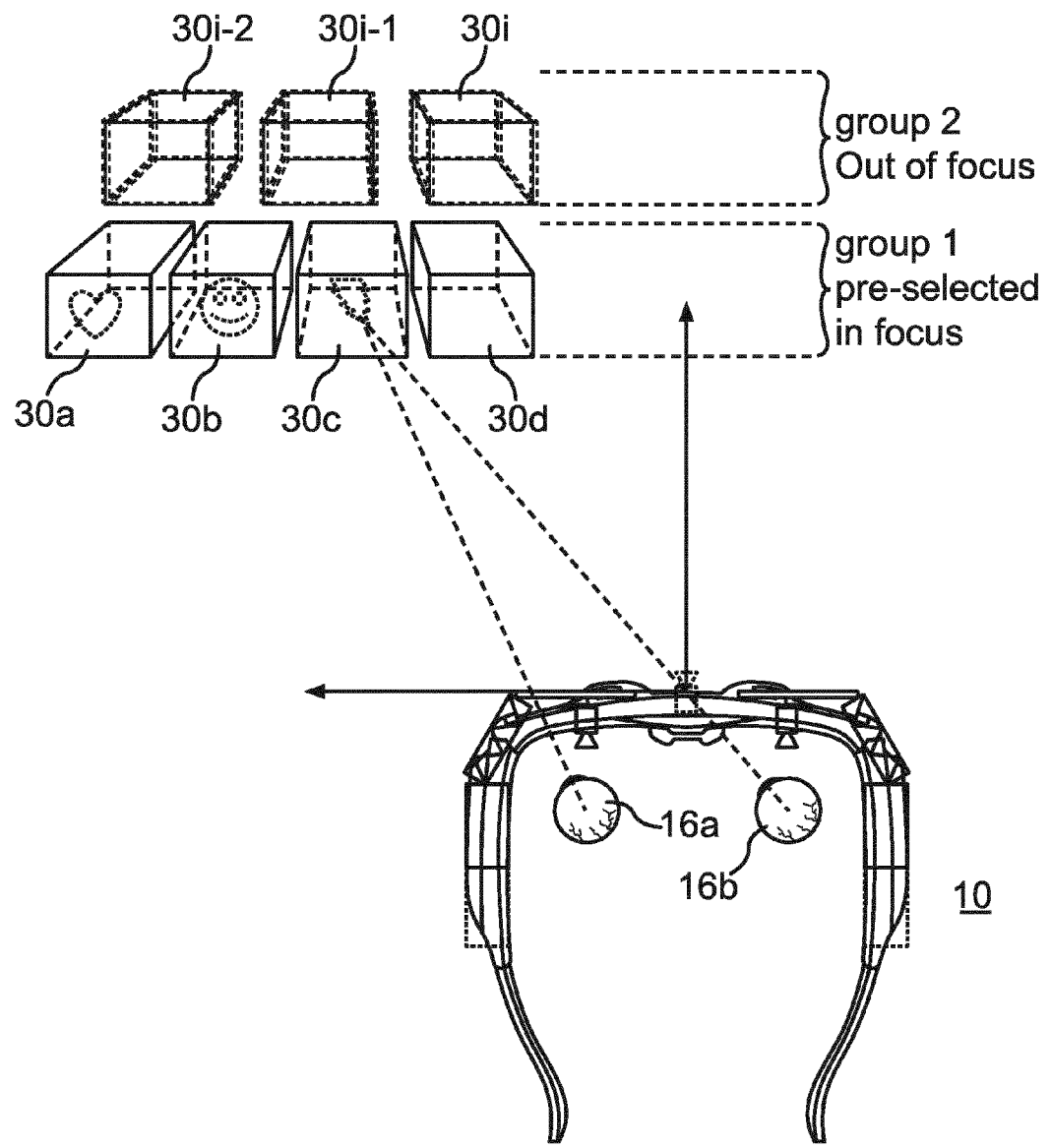

They show in:

FIG. 1a a schematic view of a first embodiment of a head mounted system according to the present invention;

FIG. 1b a schematic view of the design of an embodiment of a remotely arranged processing unit;

FIG. 2 a schematic illustration of how on the basis of the point of regard the focussing distance for each eye is determined according to the present invention;

FIG. 3 a schematic illustration of the estimation of the point of regard according to the present invention;

FIG. 4 a schematic illustration which shows objects within an in focus region determined on the basis of the point of regard in focus, whereas objects outside the in focus region are shown out of focus;

FIG. 5 a schematic illustration which shows the difference between the 3D position of the point of regard and of the calibration stimulus; and FIG. 6 a schematic illustration of how by means of a head mounted system according to the invention a first group of activation elements can be pre-selected.

FIG. 1 shows a schematic view of a first embodiment of a head mounted system 10 according to the present invention. It comprises wearing means 12, i.e. a mechanism to mount the head mounted system on a user's head, be it in the form of (but not limited to) a glasses frame or a helmet or a nose clip or an earpiece. It further comprises a binocular eye tracking system comprising a first camera 14a arranged for acquiring a user's left eye 16a, and at least a second camera 14b arranged for acquiring a user's right eye 16b. Under the term "camera" as used in the present invention all kinds of image sensors are comprised which allow capturing images of a user's eye.

Furthermore, the head mounted system can optionally comprise one or more illuminators such as LEDs, which emit invisible light, for example in the infrared spectrum, towards the user's eyes, wherein the cameras 14a, 14b are then to be adjusted to this spectrum. The head mounted system 10 further comprises a head mounted display which comprises a first light emitting array 18a and first projection means 20a for projecting an image onto a user's left eye 16a as well as a second light emitting array 18b and second projecting means 20b for projecting an image onto a user's right eye 16b. Respective light guides 22a and 22b serve the purpose of directing the respective information that is correlated with information that is to be displayed from the projection means 20a, 20b towards the light emitting arrays 18a, 18b. The light emitting arrays 18a, 18b can be opaque or transparent or partially transparent. They can be realized as a screen, for example as an LCD or AMOLED screen, i.e. any kind of displaying means which is able to present an image to the user's eye can be used by the present invention.

The head mounted system 10 further comprises processing units 24a, 24b for the left eye 16a and the right eye 16b, respectively. The processing units 24a, 24b are designed to process images from the respective camera 14a, 14b and calculate at least a 3D position of the left eye 16a and the right eye 16b and an orientation vector of the left eye 16a and the right eye 16b. The processing units 24a, 24a are also designed to compute and render a stream of digital images to be projected onto the user's left eye 16a and right eye 16b by means of the head mounted display.

While in the embodiment shown in FIG. 1a the processing units 24a, 24b are mounted to the wearing means 12, FIG. 1b indicates an embodiment in which the head mounted system 10 comprises a not shown data interface mechanically coupled to those wearing means 12, while a single processing unit 24 is coupled with said data interface in a wired or wireless manner.

In general the processing units 24, 24a, 24b preferably include a CPU and a memory and optionally co-processors to improve the speed of certain computations such as a GPU, a DSP, an FPGA or a specialized ASIC. The processing units 24a, 24b as mentioned can be integrated in the head mounted device 10 or can—as processing unit 24—be physically detached from it and connected to it through a cable or can be physically detached and communicate with the head mounted device 10 via a wireless connection, for example WIFI (802.11), Bluetooth, cellular networks such as GSM, CDMA, LTE, etc.

Additionally, the processing units 24, 24a, 24b preferably include interfaces to receive and process external data signals, such data signals including a mechanical trigger, a button or a touch-sensitive surface, an electromyographic interface connected to the body of a user, a microphone and a voice detection software, biological signals such as pulse/heart rate, blood pressure and one or more channels in a EEG interface.

The eye tracking system uses standard state of the art techniques. In a preferred embodiment to assure maximum accuracy one or more light sources emit infrared light directed towards each eye 16a, 16b, such light sources producing reflections on the cornea, called glints, which can be used as reference points to determine the eye position with respect to the respective camera 14a, 14b and together with the detected pupil contour and centre, the eye orientation.

It is otherwise possible to determine eye position and orientation without using glints and IR illuminators: For example, the eye orientation can be inferred from the perspective deformation of the pupil contour or limbus contour; the distance to the respective eye 16a, 16b can be calculated from the dimensions in the image of eye features which do not change dynamically, such as limbus maior and minor axis, or eye ball radius.

Head mounted displays are devices usually embedded with goggles or a helmet frame, which project a pair of virtual images onto the user's eyes 16*a*, 16*b*. Depending on whether the devices are designed to prevent the user's eyes 16*a*, 16*b* from seeing the environment or not, such virtual images can be used to generate an immersive experience into a simulated environment ("virtual reality") or blend simulated virtual elements within the natural environment ("augmented reality").

Traditional head mounted systems are just projection mechanisms or "screens", essentially a kind of portable personal computer monitor or TV set. The images shown can be pre-recorded videos (e.g. movie or 3D movie), or generated in real time by a computer. Regardless of whether the image content being displayed is pre-recorded or a real time generated video, at the time the images are being generated, important information about the eye of the viewer is unknown in the state of the art technologies, namely a) the position of the respective eye with respect to the screen, and the position of one eye with respect to the other eye ("intra-ocular distance"); and b) the distance and position where the respective eye is focussing its attention.

For the viewing experience to feel natural, relaxing and realistic and not to introduce strain and dizziness, the knowledge of the above-mentioned eye information is extremely important, because a) the perspective of a scene changes as the position of the respective eye 16*a*, 16*b* of the observer changes in relation to the scene; and b) depending on distance, humans' eyes change optical power, i.e. their refractive power to maintain perfect focus on the object which they are currently looking at. This process is called accommodation. Further objects and regions at different distances appear blurred or out of focus instead.

In known systems, the position of a viewer's eyes with respect to the scene shown on the head mounted system is fixed using a standard, average of the population value for eye position and intra-ocular distance. Given a certain user, the quality of his experience or the strain and dizziness that he will experience depend on how much his eyes' positions deviate from that predefined parameter or population average.

In some known devices it is otherwise possible to do a manual calibration of the head mounted system where the intra-ocular distance is manually adjusted by the user himself. This method, however, is rather coarse and it is generally impossible for the user to adjust shifts of a few degrees of rotation or a millimeter of translation.

In known systems concerning object focussing the focussing point is either decided by the video creator according to story line or artistic goals or an extended depth of focus is used where all objects in the scene appear perfectly sharp and in focus. Seeing all objects in a scene simultaneously in focus, however, is not natural, gives an impression of flatness and removes the 3D illusion. In the real world, when all objects in a scene appear in focus at the same time, it usually means that the user is looking at a 2D picture or painting.

In case only one object is in focus instead, but the focus point has been decided by the video creator, as in a movie, if the user is looking somewhere else and sees only blurriness, he will be confused or anyway the 3D illusion will be broken.

In the head mounted system according to the present invention, as mentioned an eye tracking system is used which is able to determine the 3D position of each of the user's eyes 16*a*, 16*b* with respect to the head mounted system 10. This information is then used by the processing unit 24, 24*a*, 24*b* which renders the virtual reality or augmented reality images.

The head mounted system 10 according to the present invention can be designed to perform an automatic user calibration which is then used to enhance the realism of the augmented/virtual reality experienced by the user. Each image rendered by the processing unit 24, 24*a*, 24*b* represents the scene that each user's eye 16*a*, 16*b* should see, is then rendered using as virtual camera coordinates the exact coordinates of the user's eyes 16*a*, 16*b* which have been determined by the eye tracking system.

The advantage of this approach is that the scenes which are shown to the left and right eye 16*a*, 16*b* of the user are not rendered from a fixed standard point of view in which the intra-ocular distance is based on population statistics, but are customized and optimized for each viewer, perfectly matching what the user's brain expects to see.

An optional scene camera 26 can be used to provide images of the scene the user is looking at and use those images in the context of augmented reality, as set out further below.

In addition, with a head mounted system 10 according to the present invention it is possible to determine the point of regard POR where the user's eyes 16*a*, 16*b* are focussing, which can be used to determine the focussing distance for each eye 16*a*, 16*b*, see in this regard FIG. 2.

A first way to determine such point of regard POR is to find the point of intersection of the rays originating in the user's eye positions as determined by the eye tracking system, each ray being directed according to the eye orientation determined by said eye tracking system. However, see FIG. 3, in practice in some cases such rays might not intersect in the 3D space, i.e. the rays are not coplanar. According to the present invention, the segment which represents the minimum distance between the rays is determined and the 3D position of the middle point on that segment is taken as the point of regard POR.

For users who have only one functional eye or have a strong strabismus, i.e. the brain effectively ignores the visual intake from one eye, it is still possible to determine a 3D point of regard in the virtual scene by finding the point where the ray originating from the functional eye intersects a first object in the scene.

When the 3D point of regard is known, see FIG. 4, it is possible to define an in focus region as a rectangle in which the objects are shown in focus, while objects outside of this region are shown out of focus. A particularly realistic image is obtained if objects are progressively shown out of focus as their distance from the point of regard increases.

Furthermore, it is known to those skilled in the art that there exists an offset between the so-called "line of sight" or visual axis, i.e. the imaginary line which connects the fovea, i.e. the spot of sharpest vision, and the point of regard, on the one side, and the axis which passes through the centre of the pupil, known as pupil axis or optical axis in eye tracking literature, on the other side.

While the visual axis actually represents the direction to the point of regard, as the fovea is responsible for visual intake, the eye trackers cannot see the fovea hence they can only measure the optical axis.

To compensate for the offset between visual and optical axis, which changes from person to person and for the same person changes depending on pupil dilation, emotional state and other factors, the eye tracking system can be improved by a calibration procedure to learn one or more parameters of a correction model from a set of samples.

The calibration procedure used in preferred embodiments of the present invention also provides information which is used to compensate for further sources of error or uncertainty, such as inaccuracies in the system itself, its optical components and its construction, i.e. positions, orientations and characteristics of the optical components such as camera, camera optics, etc., inaccuracies in the eye tracking algorithms and in the images, knowledge of the parameters of the user's eyes 16a, 16b, including but not limited to eye vergence defects (strabismus, lazy eye), radii of curvature of front and back surface, astigmatism, pupil aperture, limbus maior and minor axis, index of refraction of the cornea surface, index of refraction of the aqueous humor (fluid which fills the chamber between cornea and crystalline lens), radii of the crystalline lens front and back surfaces, index of refraction of the vitreus humor (fluid which fills the posterior chamber).

The set or subset of aforementioned parameters which will be object of the calibration procedure will be henceforth called the calibration parameter set.

With regard to FIG. 5, one way to realize such calibration procedure is to show to the user through the head mounted system 10 a special visual calibration stimulus 28, which the user is required to fixate. For example, such a stimulus 28 could be a dot or circle or a crosshair or any other image which is designed to attract the user's attention. This stimulus 28 corresponds to the real point of regard of the individual user. The point of regard POR shown in FIG. 5, however, corresponds to the point of regard the eye tracking system assumes.

The visual calibration stimulus can be shown at a set of discrete locations $S=\{s_1, s_2, \ldots s_m\}$, although it appears in only one specific location (taken from the set) at one specific time interval as to avoid to confuse the user. The locations can also possibly be so spatially distributed and the time interval so temporally distributed as to give the illusion of a smooth motion of the visual calibration stimulus, although that is entirely optional.

Given the set of known locations of the visual stimulus, the associated time intervals and a first inaccurate estimation of the user's point of regard on the virtual space where the visual calibration stimulus 28 is shown, the eye tracking system is calibrated by determining optimal values for the calibration parameter set which minimize the deviation between the known visual stimulus locations 28 and the point of regard POR which results from using the calibration parameter set.

More formally, given a set of parameters $p_1, \ldots p_n$ which shall be calibrated, this defines a state space for the calibration procedure $\chi=(p_1, p_2, \ldots p_n)$ e.g. as mentioned five paragraphs before.

The calibration procedure starts from a point $\chi_0$ in the state space of calibration parameters which represents a standard set of average values for the target user population and expected values for the geometrical and optical setup for the eye tracking system. Then, state of the art optimization and regression techniques are applied, for example gradient descent, Gauss-Newton, Levenberg-Marquardt, simulated annealing, evolutionary strategies etc. to find the location in the state space which minimizes a fitness function $F(\chi_i, S)$ which takes as parameters the set of stimuli locations and measured points of regard $POR_j(\chi_i)$ calculated using a set of parameters $\chi_i$, and is a measure of the deviation or error of the so-called PORs from the reference $S=\{s_1, s_2, \ldots s_m\}$.

As an example, one possible such function is the Mean Squared Error $$MSE(S, \chi_i) = \frac{1}{M} \sum_{j=1}^{M} (s_j - POR_j(\chi_i))^2.$$

It may happen under some circumstances that it is not possible to exactly match the set $S=\{s_1, s_2, \ldots s_m\}$ with a set of POR locations $POR=\{POR_1, POR_2, \ldots POR_n\}$ because $n \neq m$. In that case, it is possible to resample and interpolate the data set with the smaller number of samples to match the other set, and find a best and most likely match between samples of one set with samples of the other.

In any case, for those skilled in the art it will be trivial to use alternative fitness functions and calibration strategies depending on their actual application environment.

It is not always necessary to perform an explicit calibration showing discrete calibration stimulus images at predefined time intervals. It is generally also possible to do an implicit calibration by comparing over time a set of locations where the uncalibrated point of regard has fixated, and the paths taken between said fixations, and compare them against the scene content displayed to the user over the same period of time. This allows determining correspondences between objects and paths in the scene which are expected to attract the user focus on the one side and the actual point of regard path on the other side.

For example, if the user is being shown a text on a uniform background, he will start reading it, generating a characteristic point of regard path which will be organized in parallel lines which represent the lines of text which he is reading. It is then possible to match the point of regard path with the actual text in a way which maximizes the expected likelihood, for example using the Expectation Maximization algorithm, and then apply the aforementioned methodology to use the matched data points for calibration.

With regard to another aspect of the present invention, a 3D graphical user interface (GUI) for the head mounted display is disclosed which is controlled using the eye tracking system. In this regard, a 3D virtual activation element is defined as a finite, polygonal, 2D or 3D shape positioned at a certain 3D position with a certain 3D orientation at a certain time in the virtual space in front of the user's eyes 16a, 16b, being rendered by the processing unit 24, 24a, 24b and displayed by the head mounted display.

With regard to FIG. 6 3D virtual activation elements 30 are shown which can be of varying colour, may contain text or an image in themselves and may have varying degrees of transparency. They may be completely opaque and block the view of scene elements behind them or they can be fully transparent (hence invisible) or can have any degree of translucency in between.

A 3D virtual activation element 30 is associated with the activation of one or more functions in the user interface, for example the activation of applications (launching a web browser or email client, etc.) or represent a (data) file in the file system of a computer connected to the head mounted system (for example, a video or sound file).

Such 3D virtual activation element 30 can be associated with an event or trigger the use of a certain function or method on the processing unit 24, 24a, 24b, if a certain activation condition is met or the event can be associated with the sequential activation of several virtual activation elements 30: For example, one possibility would be to first activate a video element, followed by activating a video-player element, to trigger the playback of the activated video.

The activation condition itself can be performed in many possible ways:

In one possible embodiment, the activation is triggered when the user's point of regard enters the virtual space defined by the 3D virtual activation element 30, as can be seen in FIG. 6 with regard to activation element 30*c*. It is otherwise possible that the activation occurs when the user's point of regard enters the virtual space defined by the 3D virtual activation element 30 and dwells within that space for a predefined amount of time. It is otherwise possible that the activation occurs when the user's point of regard enters the virtual space defined by the 3D virtual activation element 30 and dwells within that space for a predefined dwell time and then exits that space within a predefined exit time. It is otherwise possible that the activation occurs when the user's point of regard enters the virtual space defined by the 3D virtual activation element 30 and subsequently the user intentionally blinks the eyes to trigger the activation.

Since blinking is otherwise a naturally occurring event and most people cannot stay a long time without blinking, it is possible to define a time window (minimum, maximum) within which the intentional, activating blink is allowed to occur; blinks outside of this time window will be simply ignored.

It is otherwise possible to include external triggering signals which do not originate from the eye tracking system itself but which work in combination with the eye tracking system to activate a certain function. Such external signals can be (but are not limited to):

- the pushing of a mechanical trigger or button (for example like on a keyboard or mouse or a mechanical button integrated or connected by a cable or wirelessly to the head mounted system 10) or touching a touch sensitive interface (such as a resistive or capacitive touchpad or a digitizer);
- the change of signals measured by an electromyographic interface (EMG) connected to the user's body, which matches a certain pattern; an electromyographic interface measures electrical activity in the muscles and is a consequence of the activation of motor neurons; a surface-EMG can be used by anybody, for example worn on the arm, but this type of interface can be of particular relevance for people with disabilities and amputees, also in the form of intramuscular EMG using electrodes; the recognition of activation patterns can be done by training a machine learning classifier, for example using an artificial neural network or support vector machine; using this interface, it is then possible to activate a 3D virtual activation element 30 in the GUI by contracting or relaxing a muscle in the body, for example in the arm, and this has the advantage of leaving the user's hands free;
- a voice command, for example the commands "play" or "start", is issued by the user and recognized by the system using a voice recognition software and a microphone;
- a finger, hand or arm gesture, recognized by a motion sensing device (Kinect, Leap Motion, etc.), for example performing an activation by swiping a hand or pinching with fingers, etc;
- one or more biological monitoring functions reach a threshold level, such biological levels can represent a certain physical state (fatigue, rest, etc.) or emotional state (arousal, relaxation, stress, happiness, fear, etc.); such biological monitoring functions can be signals from an Electroencephalography (EEG) which monitors brain electrical activity; Electrocardiography (EKG) which monitors heart electrical activity; heart pulse rate; blood pressure; pupil dilation; so, for example, it would be possible to activate a function by concentrating and "thinking" about it, or have another function where a different music and video is played depending on the mood of the user, or a visual feedback can be given to the user, suggesting to slow down while jogging if excessive fatigue is detected.

By further reference to FIG. 6 the 3D virtual activation elements 30 can be arranged in groups where elements in a group can perform closely related functionality (for example, open email, compose email, delete email) and be located in the virtual space close to each other and within a narrow distance range from the eyes. With regard to FIG. 6, a first group is formed by activation elements 30*a*-30*d*, while a second group of activation elements is formed by activation elements $30_{i-2}$, $30_{i-1}$ and $30i$. It is possible then to highlight a specific group by rendering all the 3D virtual activation elements 30*a* to 30*d* within "in focus", while the elements $30_{i-2}$, $30_{i-1}$, $30i$ of the other groups will be "out of focus" and can optionally become increasingly translucent (partially or completely transparent) so as not to occlude, distract or interfere with the view of the highlighted group.

This way a group of activation elements 30*a* to 30*d* can be pre-selected, for example when the user focuses on one 30*c* of them and the detected point of regard lies within its boundaries. Then all other elements 30*a*, 30*b*, 30*d* which belong to the same group can be pre-activated (put "in focus", and optionally be readied to fire the associated events).

In this way it is possible to organize the 3D GUI as a layered interface, where each layer contains one or more groups of activation elements 30 and the user is able to navigate through the different layers simply by focussing his gaze at different distances.

As a special case of the approach described here, it is also possible to represent the activation elements 30 as simple 2D planar objects, all lying on the same virtual plane in the 3D scene. This way effectively realizes a 2D user interface for the 3D virtual/augmented reality system. The 3D user interface has obvious advantages in terms of power and flexibility, but in some applications the 2D interface might be preferable due to its simplicity.

In order to improve known head mounted systems, the present invention in particular allows for an optimal positioning of the virtual camera on the one hand as well as an optimal, realistic focussing of the virtual camera. In the former case it is taken into account what the image looks like depending on the 3D position of the eyes which look at the scene, whereas in the latter case the focus is realistically adjusted around the point looked at by the eyes.

The invention claimed is:

1. A head mounted system (10) comprising:
a) a binocular eye tracking system (14*a*, 14*b*) comprising:
at least a first camera (14*a*) arranged for acquiring a user's left eye (16*a*);
at least a second camera (14*b*) arranged for acquiring a user's right eye (16*b*);
b) a head mounted display (10) comprising:
a first displaying means (18*a*) for presenting an image to a user's left eye (16*a*);
a second displaying means (18*b*) for presenting an image to a user's right eye (16*b*);
c) a processing unit (24, 24*a*, 24*b*) designed to
process images from the eye tracking system (14*a*, 14*b*) and calculate at least an orientation vector of the left (16*a*) and the right eye (16*b*);

characterized in that the processing unit (24, 24a, 24b) is further designed to
calculate a 3D position of the left (16a) and the right eye
(16b);
compute and render a stream of digital images to be
projected onto the user's left and right eye (16a, 16b)
by means of the head mounted display; and
consider the 3D position of the left and the right eye
(16a, 16b) and the orientation of the left and the right
eye (16a, 16b) when computing and rendering the
stream of digital images for positioning a virtual camera when rendering a virtual 3D scene and/or to determine which part of a virtual scene is rendered in focus.

2. The head mounted system (10) according to claim 1, characterized in that
the head mounted system (10) comprises wearing means (12) and the processing unit (24, 24a, 24b) is mechanically coupled to those wearing means (12).

3. The head mounted system (10) according to claim 1, characterized in that
the head mounted system (10) comprises wearing means (12) and a data interface mechanically coupled to those wearing means (12), the processing unit (24, 24a, 24b) being coupled with said data interface, especially wired or wireless.

4. The head mounted system (10) according to claim 1, characterized in that
the head mounted system (10) comprises light guide means for projecting images onto said user's eyes (16a, 16b), which follow a substantially separate optical path as the optical path used by the eye tracking system (14a, 14b).

5. The head mounted system (10) according to claim 1, characterized in that
the processing unit (24, 24a, 24b) is designed to calculate the 3D position of a point of regard (POR), in particular the 3D position of the point of regard (POR) and the distances to each of the eyes (16a, 16b), that the user is fixating using the 3D eye position of the left and the right eye (16a, 16b) and the orientation vectors of the left and the right eye (16a, 16b).

6. The head mounted system (10) according to claim 1, characterized in that
the processing unit (24, 24a, 24b) is designed to estimate the 3D position of the point of regard (POR) as the closest point between the left and the right direction rays defined by the calculated 3D positions and orientation vectors of the left and the right eye (16a, 16b), if the left and the right direction rays do not intersect.

7. The head mounted system (10) according to claim 6, characterized in that
the processing unit (24, 24a, 24b) is designed to filter the left and the right eye direction rays and positions through a mapping function, especially by applying an offset, a linear or a non-linear transformation.

8. The head mounted system (10) according to claim 7, characterized in that
the processing unit is designed to carry out a calibration procedure calibrating the head mounted system (10) for a specific user, wherein the mapping function is the result of the calibration procedure.

9. The head mounted system (10) according to claim 8, characterized in that
the processing unit (24, 24a, 24b) is designed to carry out the calibration procedure by showing through the head mounted display to the user virtual stimuli (28), in particular virtual targets, to be fixated and determining the difference between the point of regard (POR) calculated by the 3D positions and orientation vectors of the left and the right eye (16a, 16b) on the one side and the location of said virtual stimuli (28).

10. The head mounted system (10) according to claim 9, characterized in that
the processing unit (24, 24a, 24b) is designed to provide said virtual targets (and/or stimuli (28)) moving along a predetermined or random path.

11. The head mounted system (10) according to claim 9, characterized in that
the processing unit (24, 24a, 24b) is designed to carry out the calibration procedure by continuously calculating over time the difference between the point of regard (POR) calculated by the 3D positions and orientation vectors of the left and the right eye (16a, 16b) on the one side and frequent objects of interest and/or visual anchors in the images projected on the head mounted display.

12. The head mounted system (10) according to claim 5, characterized in that
the processing unit (24, 24a, 24b) is designed to calculate the intra-ocular distance and is further designed to calculate based on the intra-ocular distance and the 3D positions of the left and the right eye (16a, 16b) the virtual points of view and to use these virtual points of view when rendering a pair of images for the left and the right eye (16a, 16b) for simulating a 3D virtual scene.

13. The head mounted system (10) according to claim 5, characterized in that
the processing unit (24, 24a, 24b) is designed to determine based on the distance of the point of regard (POR) a region which is to be shown in focus in the rendered virtual image, wherein the processing unit (24, 24a, 24b) is further designed to render the virtual images accordingly to simulate the depth of focus for the whole image which a human eye would observe if it were seeing a real object at the same 3D coordinates as the point of regard (POR) in a real scene.

14. The head mounted system (10) according to claim 13, characterized in that
the processing unit (24, 24a, 24b) is designed to render based on the 3D positions of the left and the right eye (16a, 16b) on the one side and the distance to said point of regard (POR) on the other side at least one augmented reality element which blends in with the scene as seen by a user wearing the head mounted system (10).

15. The head mounted system (10) according to claim 1, characterized in that
the processing unit (24, 24a, 24b) is designed to render at least one virtual activation element (30) to be shown in the images, especially the images of a scene, projected onto the user's eyes (16a, 16b), the processing unit (24, 24a, 24b) being further designed to activate a predetermined function associated with the virtual activation element (30) if a predetermined activation condition is met.

16. The head mounted system (10) according to claim 1, characterized in that
the processing unit (24, 24a, 24b) is designed to render said at least one virtual activation element (30) as a finite, polygonal, 3D shape positioned at a predetermined position with a predetermined 3D orientation for a certain time in the scene.

17. The head mounted system (10) according to claim 15, characterized in that
the processing unit (24, 24a, 24b) is designed to render said at least one virtual activation element (30) with a predetermined colour and/or containing text and/or an image in itself and/or with varying degrees of transparency between none and fully transparent.

18. The head mounted system (10) according to claim 15, characterized in that
the processing unit (24, 24a, 24b) is designed to render said at least one virtual activation element (30) with varying degrees of transparency between none and fully transparent dependent on a distance of a focused gaze of the user.

19. The head mounted system (10) according to claim 15, characterized in that
the processing unit (24, 24a, 24b) is designed such that the activation condition consists in the 3D point of regard (POR) entering a virtual space region defined by the activation element (30).

20. The head mounted system (10) according to claim 15, characterized in that
the processing unit (24, 24a, 24b) is designed such that the activation condition consists in the 3D point of regard (POR) dwelling in the virtual space region defined by the activation element (30) for a predetermined amount of time.

21. The head mounted system (10) according to claim 15, characterized in that
the processing unit (24, 24a, 24b) is designed such that the activation condition consists in the 3D point of regard (POR) entering and exiting the virtual space region defined by the activation element (30) within a predetermined amount of time.

22. The head mounted system (10) according to claim 15, characterized in that
the processing unit (24, 24a, 24b) is designed such that the activation condition consists in the 3D point of regard (POR) entering the virtual space region defined by the activation element (30) and a subsequent blink within a predetermined time window being detected by the eye tracking system (14a, 14b).

23. The head mounted system (10) according to claim 15, characterized in that
the processing unit (24, 24a, 24b) is designed such that the activation condition consists in the 3D point of regard (POR) entering the virtual space region defined by the activation element (30) and a subsequent trigger event from an external interface is being activated.

24. The head mounted system (10) according to claim 23, characterized in that
the trigger event from an external interface being:
the pushing of a mechanical trigger, button or touch sensitive surface;
the detection of a change in an electromyographic interface connected to the body of the user;
the issuing of a voice command;
a biological monitoring function reaching a threshold level, the biological monitoring function especially consisting in pulse/heart rate, blood pressure, a channel in an EEG interface; and/or
a finger, hand or arm gesture detected by a gesture sensor.

25. The head mounted system (10) according to claim 1, characterized in that
the processing unit (24, 24a, 24b) is designed to highlight and/or pre-activate a group of activation elements (30a to 30d) which lie at the same virtual distance based on an image disparity and a simulated depth of focus calculated from the 3D positions of the left eye (16a), the right eye (16b) and the point of regard (POR).

26. The head mounted system (10) according to claim 1, characterized in that
the processing unit (24, 24a, 24b) is designed to highlight and/or pre-activate a group of all activation elements (30a to 30d) which lie at the same virtual distance based on an image disparity and a simulated depth of focus calculated from the 3D positions of the left eye (16a), the right eye (16b) and the point of regard (POR).

27. The head mounted system (10) according to claim 25, characterized in that
the processing unit (24, 24a, 24b) is designed to highlight a certain group of activation elements (30a to 30d) by substantially focussing all its elements, while all other activation elements ($30_{i-2}, 30_{i-1}, 30_i$) in other groups are being rendered out of focus.

28. The head mounted (10) system according to claim 27, characterized in that
the processing unit (24, 24a, 24b) is designed to further render all other activation elements ($30_{i-2}, 30_{i-1}, 30_i$) in other groups partially or completely transparent.

29. The head mounted system (10) according to claim 1, characterized in that
the processing unit (24, 24a, 24b) is designed to calculate the 3D position of the left (16a) and the right eye (16b) with respect to the respective camera (14a; 14b), wherein a distance of the respective camera (14a; 14b) to the respective eye (16a; 16b) is calculated from the dimensions in the image of eye features which do not change dynamically.

30. A method to compute and render a stream of digital images using a head mounted system (10) comprising a binocular eye tracking system (14a, 14b) with at least a first camera (14a) arranged for acquiring a user's left eye (16a) and at least a second camera (14b) arranged for acquiring a user's right eye (16b); a head mounted display with a first displaying means (18a) for presenting an image to a user's left eye (16a) and a second displaying means (18b) for presenting an image to a user's right eye (16b); and a processing unit (24, 24a, 24b) designed to process images from the eye tracking system (14a, 14b) and calculate at least an orientation vector of the left and the right eye (16a, 16b);
characterized by the following steps:
the processing unit (24, 24a, 24b) calculates a 3D position of the left and the right eye (16a, 16b);
the processing unit (24, 24a, 24b) computes and renders a stream of digital images to be projected onto the user's left and right eye (16a, 16b) by means of the head mounted display; and
considering the 3D position of the left and the right eye (16a, 16b) and the orientation of the left and the right eye (16a, 16b) when computing and rendering the stream of digital images for positioning a virtual camera when rendering a virtual 3D scene and/or to determine which part of a virtual scene is rendered in focus.

* * * * *